United States Patent [19]

Mardin et al.

[11] Patent Number: 4,670,460
[45] Date of Patent: Jun. 2, 1987

[54] INHIBITING LIPOXYGENASE WITH PYRAZOLONE DERIVATIVES

[75] Inventors: Mithat Mardin, West Haven, Conn.; Friedel Seuter, Wuppertal; Elisabeth Perzborn, Wuppertal; Klaus Schlossmann, Wuppertal; Dieter Mayer, Werne; Volker Fiedler, Wuppertal, all of Fed. Rep. of Germany

[73] Assignee: Bayer Aktiengesellschaft, Leverkusen, Fed. Rep. of Germany

[21] Appl. No.: 808,582

[22] Filed: Dec. 13, 1985

Related U.S. Application Data

[60] Division of Ser. No. 609,933, May 14, 1984, abandoned, which is a continuation-in-part of Ser. No. 486,176, Apr. 18, 1983, abandoned.

[30] Foreign Application Priority Data

Mar. 12, 1983 [DE] Fed. Rep. of Germany ....... 3308881
Nov. 25, 1983 [DE] Fed. Rep. of Germany ....... 3342628

[51] Int. Cl.[4] ........................................ A61K 31/415
[52] U.S. Cl. .................................................. 514/404
[58] Field of Search ......................................... 514/404

[56] References Cited

U.S. PATENT DOCUMENTS

| | | | |
|---|---|---|---|
| 3,147,276 | 9/1964 | Drain et al. ........................ | 548/367 |
| 4,053,621 | 10/1977 | Möller et al. ..................... | 424/273 P |
| 4,099,011 | 7/1978 | Möller et al. ..................... | 548/376 |
| 4,113,957 | 9/1978 | Möller et al. ..................... | 548/377 |
| 4,418,079 | 11/1983 | Kojima et al. ..................... | 424/330 |
| 4,472,428 | 9/1984 | Toru et al. ........................ | 424/285 |
| 4,478,842 | 10/1984 | Renfroe ............................. | 424/263 |
| 4,479,949 | 10/1984 | Iwao et al. ........................ | 424/248 |

Primary Examiner—Leonard Schenkman
Attorney, Agent, or Firm—Sprung Horn Kramer & Woods

[57] ABSTRACT

A method of inhibiting lipoxygenase in a patient, for the prophylaxis and/or treatment of ischaemias and disorders in cardiac rhythm, inflammations of the skin and the eye, and of rheumatic, allergic and asthmatic diseases, oedemas, pulmonary embolisms, pulmonary hypertension, shock lung, oxygen intoxications and ulcerations which comprises administering to such patient an effective amount of a compound of the formula

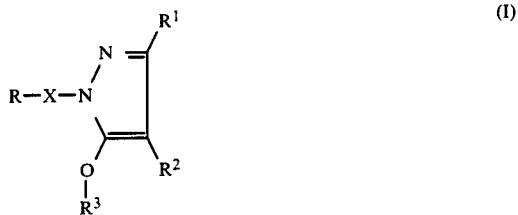

wherein
R represents an aryl or heteroaryl radical which has 6 to 12 C atoms and optionally contains 1 to 3 identical or different substituents from the group comprising halogen, trifluoromethyl, alkyl, alkenyl, alkoxy, alkylamino, cyano, trifluoromethoxy, nitro, hydroxyl, $SO_n$-alkyl (n=0 to 2) or $SO_n$-trifluoromethyl (n=0 to 2), alkyl, alkenyl and alkoxy in each case being understood as meaning radicals with 1 to 4 C atoms, $R^1$ represents hydrogen or a hydrocarbon radical which has 1 to 18 C atoms and optionally contains a hydroxyl, ether, ester or carboxyl group and optionally 1 to 3 halogen atoms, $R^2$ has the meaning of $R^1$ or represents radical

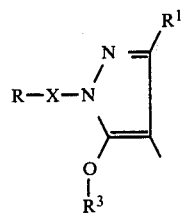

$R^3$ represents hydrogen or an acyl or sulphonyl radical with in each case 1 to 15 C atoms and X represents one of the groups $-O-CH_2-CH_2-$, $-S-CH_2-CH_2-$, $-CH_2-CH_2-CH_2-$, $-CH_2-CH_2-$, $-CH_2$ or

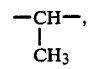

the oxygen or sulphur atom being bonded to the radical R, and with the provisio that X does not represent $-O-CH_2-CH_2-$ if R=β-naphthyl, $R^1=CH_3$ and $R^2=R^3=H$.

11 Claims, No Drawings

INHIBITING LIPOXYGENASE WITH PYRAZOLONE DERIVATIVES

This is a division of Application Ser. No. 609,933, filed May 14, 1984, now abandoned, which in turn is a continuation-in-part of Application Ser. No. 486,176, filed Apr. 18, 1983, now abandoned.

The present invention relates to the use of certain 1-substituted pyrazol-5-one derivatives as lipoxygenase inhibitors for the prophylaxis and treatment of ischaemias, in particular of cardiac infarctions following myocardial ischaemias, and disorders in cardiac rhythm, inflammations of the skin (in particular psoriasis) and inflammations of the eye, rheumatic, allergic and asthmatic diseases, pulmonary embolisms, shock lung and oedemas (in particular pulmonary oedemas), pulmonary hypertension, oxygen intoxications and ulcerations. The invention also relates to medicaments for inflammations of the skin and eye and shock lung, and lipoxygenase-inhibiting, bronchodilatory antiarrhythmic, antiischaemic, antirheumatic, antiallergic, antiasthmatic, antioedemic and gastroprotective medicaments which are characterized in that they contain a therapeutically active amount of the pyrazolone derivative.

U.S. Pat. No. 3,147,276 states that certain 1-substituted pyrazol-5-ones have antiinflammatory properties. It is also known that numerous pyrazol-5-one derivatives can be used as diuretic agents, antihypertensive agents and antithrombotic agents (DE-OS [German Published Specification] No. 2,319,280, DE-OS [German Published Specification] No. 2,554,701, DE-OS [German Published Specification] No. 2,363,511 and DE-OS [German Published Specification] No. 2,554,703).

By far the most powerful antithrombotic agent has proved to be 3-methyl-1-[2-(2-naphthyloxy)-ethyl]-2-pyrazolin-5-one ("nafazatrom"), which is described in DE-AS [German Published Specification] No. 2,247,272 (U.S. Pat. No. 4,053,621). It has also been disclosed that nafazatrom can act as a stimulator of endogenous prostacyclin (PGI$_2$) from the vascular endothelium (Vermylen et al., Lancet I, 528, 1979, Chamone et al., Haemostasis 10, 297, 1981 and McIntyre and Salzman, Thrombosis and Haemostasis, 46, Abstract No. 45, 1981). Wong and McGiff (J. Pharmacol. Exp. Ther. 223, 757-760, 1982) have also shown that nafazatrom blocks 15-hydroxyprostaglandin dehydrogenase, the PGI$_2$-degrading enzyme.

Moreover, the substance inhibits lipoxygenase activity (Busse et al., Fed. Proc. 41, 1717, 1982).

As has been found, the antithrombotic action of nafazatrom is exceptionally dependent on the structure: as, for example, replacement of methyl by ethyl in the 3-position of nafazatrom reduces its action in the prophylaxis of thromboses to about 1/30th, while no effect can be detected with the corresponding 3-benzyl, 3-isopropyl, 3-n-propyl or 3,4-dimethyl derivative, even when the dose is increased 100 times in comparison with nafazatrom. It is therefore to be regarded as extremely surprising that these compounds and also pyrazolone derivatives, which are even more distant from a structural point of view, are at least equivalent to nafazatrom in respect of the other abovementioned action qualities.

The pyrazolone derivatives to be used according to the invention correspond to the general formula

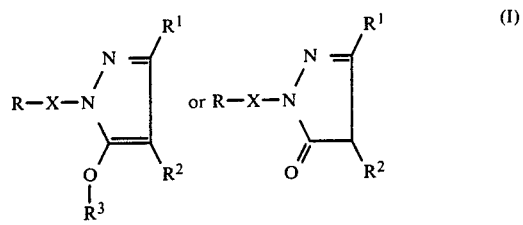

wherein

R represents an aryl or heteroaryl radical which has 6 to 12 C atoms and optionally contains 1 to 3 identical or different substituents from the group comprising halogen, trifluoromethyl, alkyl, alkenyl, alkoxy, alkylamino, cyano, trifluoromethoxy, nitro, hydroxyl, SO$_n$-alkyl (n=0 to 2) or SO$_n$-trifluoromethyl (n=0 to 2), alkyl, alkenyl and alkoxy in each case being understood as meaning radicals with 1 to 4 C atoms, R$^1$ represents hydrogen or a hydrocarbon radical which has 1 to 18, preferably 1 to 8, C atoms and optionally contains a hydroxyl, ether, ester or carboxyl group and optionally 1 to 3 halogen atoms, R$^2$ has the meaning of R$^1$ or represents a radical

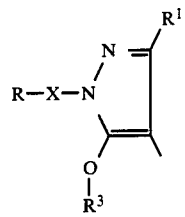

R$^3$ represents hydrogen or an acyl or sulphonyl radical with in each case 1 to 15 C atoms and X represents one of the groups —CH$_2$—CH$_2$—CH$_2$—, —O—CH$_2$—CH$_2$—, —S—CH$_2$—CH$_2$—, —CH$_2$—CH$_2$—, —CH$_2$ or

—CH—,
|
CH$_3$ the oxygen or sulphur atom being bonded to the radical R, and with the proviso that X does not represent —O—CH$_2$—CH$_2$— if R=β-naphthyl; R$^1$=CH$_3$ and R$^2$=R$^3$=H.

Compounds of the general formula (I) which are preferably to be employed according to the invention are those in which R represents an optionally substituted naphthyl, diphenyl or phenyl radical, particularly preferably a naphthyl or diphenyl radical, especially α- or β-naphthyl. These radicals preferably carry 0, 1 or 2 substituents, in particular Br or Cl. Bromonaphthyl radicals are particularly preferred.

Compounds of the general formula (I) which are furthermore preferred according to the invention are those in which R$^1$ represents a phenyl, benzyl or cyclohexyl radical, or an aliphatic hydrocarbon radical, preferably a radical with 1 to 4 C atoms, which optionally carries a hydroxyl, ether or ester group, particularly preferably an optionally branched C$_1$-C$_4$-alkyl group, and $R^2$ has the preferred meaning of $R^1$ or represents hydrogen. Particularly preferably, at least one of the radicals $R^1$ or $R^2$ is not hydrogen and $R^1$ and $R^2$ together have 2 to 7, in particular to 2 to 4, C atoms.

Compounds of the general formula (I) which are furthermore preferred according to the invention are those in which $R^3$ represents hydrogen or an aromatic acyl radical which has 7 to 13 C atoms, in particular a carboxyphenyl or carboxynapthyl radical, and which optionally contains 1 or 2 substituents from the group comprising halogen, trifluoromethyl, $C_1$–$C_4$-alkoxy and nitro. $R^3$ is particularly preferably hydrogen.

Finally, compounds which are preferred according to the invention are also those in which X represents —O—$CH_2$—$CH_2$—, —S—$CH_2$—$CH_2$—, —$CH_2$—$CH_2$— —$CH_2$—$CH_2$—$CH_2$— or

—CH—,
|
$CH_3$ in particular —O—$CH_2$—$CH_2$—, —$CH_2$—$CH_2$—$CH_2$— or

—CH—
|
$CH_3$ if $R^3$ = H, besides in the form represented by formula (I), the compounds to be employed according to ntion the invention can also be in one of the following tautomeric forms or as a mixture of the possible tautomeric forms:

$$\underset{R-X-N}{\overset{H\diagdown N\diagup R^1}{\phantom{xx}}}\phantom{xxx}\text{(Ia)}$$

$$\underset{R-X-N}{\overset{N=R^1}{\phantom{xx}}}\phantom{xxx}\text{(Ib)}$$

The pyrazolone derivatives of the general formula (1) to be employed according to the invention are known from DE-OS [German Published Specification] No. 2,319,280 (U.S. Pat. No. 3,957,814), DE-OS [German Published Specification] No. 2,363,511 (U.S. Pat. No. 4,002,641), DE-OS [German Published Specification] No. 2,554,701 and DE-OS [German Published Specification] No. 2,554,703, and they can be prepared by the processes described in detail therein.

Compounds of the formula (I) in which $R^3$=H are obtained by a process in which
(A) hydrazines of the formula

R—X—NH—NH$_2$ (II)

in which R and X have the abovementioned meaning, are reacted with α-keto acid derivatives of the formula $$R^1-\underset{\underset{R^2}{|}}{C(=O)}-CH-C(=O)-Y \quad \text{(III)}$$

in which
$R^1$ and $R^2$ have the abovementioned meaning and
Y represents a leaving radical, for example a hydroxyl, alkoxy, aralkoxy, amino or alkylamino radical,
if appropriate in the presence of inert solvents and basic or acid catalysts, such as alkali metal and alkaline earth metal hydroxides and carbonates, or such as hydrogen halide acids, sulphuric acid or sulphonic acids, at temperatures between 10° and 200° C., or
(B) compounds of the formula

R—X—A (IV)

in which
R has the abovementioned meaning and
A represents a leaving radical, such as halogen or a dialkyloxonium, dialkylsulphonium or trialkylammonium radical or an aryl- or trifluoromethyl-sulphonic acid radical,
with pyrazol-5-one derivatives of the formula (V)

in which $R^1$ and $R^2$ have the abovementioned meaning, if appropriate in the presence of inert solvents and inorganic or organic bases, such as alkali metal hydroxides, carbonates, alcoholates, hydrides or amines, at temperatures between 10° and 200° C., or
(C) acetylenecarboxylic acid derivatives of the formula $$Y-\overset{O}{\underset{\|}{C}}-C\equiv C-R^1 \quad \text{(VI)}$$

in which $R^1$ and Y have the abovementioned meaning, are reacted with hydrazines of the above formula (II), if appropriate in the presence of inert solvents and inorganic or organic bases, at temperatures between 50° and 200° C.

Compounds of the formula (I) in which $R^3\neq H$ are obtained by a process in which a compound of the formula in which R, X, R¹ and R² have the abovementioned meaning, are reacted with acid derivatives, preferably with (a) carboxylic or carbonic acid derivatives of the formula

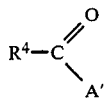 (VII)

in which A' denotes a leaving radical, such as halogen, or a 5-membered, heterocyclic azole ring, or an alkyl group bonded to the carbonyl carbon by an oxygen or sulphur atom, or a phenyl radical which is optionally substituted by 1 or 2 nitro groups, or an acyloxy radical and R⁴—C=O has the meaning of R³, or (b) with sulphonic acid derivatives of the formula

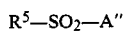 (VIII)

in which R⁵—SO₂ has the meaning of R³ and A" represents halogen, if appropriate in the presence of inert solvents and basic auxiliaries, such as alkali metal or alkaline earth metal hydroxides and carbonates or organic bases, such as triethylamine or pyridine, at temperatures between −20° and 150° C.

Surprisingly, the pyrazolone derivatives to be employed according to the invention inhibit lipoxygenase activity, which is responsible for the biosynthesis of the chemotactically active leukotriene B₄ and the spasmogenically active leukotrienes C₄ and D₄.

Known lipoxygenase inhibitors, such as nordihydroguaiaretic acid, 3-amino-1-(3-trifluoromethylphenyl)-pyrazoline (BW 755 C), phenidone and 5,8,11,14-eicosatetranoic acid, have the disadvantage that they are either at the same time active as cyclooxygenase inhibitors or active only in very high concentrations. Inhibition of the enzyme cyclooxygenase from the metabolism of arachidonic acids leads to a global inhibition of prostaglandin synthesis and to a stimulation of the lipoxygenase path, which can cause gastrotoxicity, inflammation-promoting and asthmatic actions and an increased tendency towards thromboses as a result of inhibition of prostacyclin synthesis.

No such inhibition of cyclooxygenase occurs on administration of the pyrazolone derivatives to be used according to the invention. In contrast, these derivatives exhibit a marked antiasthmatic, inflammation-inhibiting and gastro-protective action.

Surprisingly, the pyrazolone derivatives to be used according to the invention selectively inhibit the 5-lipoxygenase responsible for biosynthesis of the leukotrienes B₄, C₄ and D₄, while the 15-lipoxygenase responsible for biosynthesis of the endogenous lipoxygenase inhibitors 15-hydroxyeicosatetraenoic acid (15-HETE) is not inhibited or is even stimulated at concentrations of 10 ug/ml. Likewise, the 12-lipoxygenase activity is not inhibited by these concentrations of the pyrazolone derivatives to be used according to the invention. Furthermore, the pyrazolone derivatives to be used according to the invention specifically stimulate synthesis of prostacyclin (PGI₂).

Surprisingly, only PGI₂ synthesis is stimulated in the presence of the pyrazolone derivatives to be employed according to the invention, while synthesis of vasoconstrictory prostaglandins and TXA₂ is not influenced. The pyrazolone derivatives to be employed according to the invention also display vasodilating effects locally, these being particularly of therapeutic use in ischaemic tissue (for example heart, brain and periphery). In contrast to indomethacin, which has an overall inhibiting action on the synthesis of prostaglandins from arachidonic acid, the pyrazolone derivatives to be employed according to the invention intervene much more specifically in the metabolism of the enzymes decisive for the formation of PGI₂, thromboxan and the leukotrienes, so that not only is the harmful, vasoconstricting and arrhythmia-increasing influence of thromboxan and the leukotrienes reduced, but also the vasodilating influence of the prostacyclin is increased by stimulation of its formation.

In addition, the pyrazolone derivatives to be employed according to the invention reduce or exclude the harmful effect of a sudden influx of oxygen following a hypoxic or anoxic period. Damage by reoxygenation can occur after bypass operations. The pyrazolone derivatives to be employed according to the invention are therefore suitable for preventing oxygen damage in such operations.

Surprisingly, it has also been found that the pyrazolone derivatives according to the invention reduce the stickiness of leucocytes, that is to say they increase their rate of migration. This reduction in the stickiness of leucocytes likewise contributes to a decrease in ischaemic areas, since, after treatment with the pyrazolone derivatives to be employed according to the invention, the leucocytes pass through the microcirculatory area of these regions without causing restricted supply to corresponding tissues as a result of total or temporary closure of small vessels or capillaries.

The pyrazolone derivatives to be employed according to the invention can moreover also be used for the therapy of pulmonary hypertension, pulmonary embolisms, pulmonary oedemas and shock lung (ARDS="Adult Respiratory Distress Syndrome"). The bronchodilating properties of the active compounds can be demonstrated, for example, on isolated lungs of guinea pigs (by the method F. P. Luduene et al., Arch. Int. Pharmacodyn. 111, 392, 1957).

The compounds to be used according to the invention are also suitable for the therapy of inflammations of the eye and skin, in particular psoriasis and vitiligo.

The pyrazolone derivatives to be employed according to the invention furthermore surprisingly reduce the size of cardiac infarctions following myocardial ischaemias, and have a positive influence on disorders in cardiac rhythm. These intended uses according to the invention of the pyrazolone derivatives to be employed according to the invention are also not suggested by the abovementined indications known from the prior art:

Substances for the therapy of disorders in cardiac rhythm are classified according to their electrophysiological actions.

Since the classification of Vaughan Williams (Pharmac. Ther. B 1, 115, 1975), the following classes are differentiated:

(I) Membrane-stabilizing antiarrhythmic agents of
  (a) the quinidine type, for example procaine and ajmaline, and
  (b) the lidocaine type, for example lidocaine and diphenylhydantoin
(II) Beta-receptor blockers, such as, for example, propanolol and many others.
(III) Calcium antagonists, such as, for example, verapamil, nifedipine and many others.

(IV) Substances with an increase in the duration of action potential, such as, for example, amiodarone.

The pyrazolone derivatives to be employed according to the invention cannot be sub-classified under the above groups either on the basis of their chemical structure or on their actions known hitherto. For this reason, it could not be predicted that the pyrazolone derivatives to be employed according to the invention display antiarrhytmic effects. On the basis of the antithrombotic action, it was just as unlikely that the pyrazoline derivatives to be employed according to the invention greatly would restrict the spread of myocardial ischaemia after vascular occlusion—and in particular independently of the nature of the occlusion of the coronary vessel—and thus reduce the size of infarction and moreover lead to more rapid healing and fewer side effects on the circulation. As can be demonstrated by animal experiments, the pyrazolone derivatives to be employed according to the invention reduce the ischaemia-induced rise in the S zone as an indication of infarction; moreover, the R-wave in the ECG of the peripheral extremities increases less sharply and re-forms more rapidly; ST intervals are changed less than in the controls, which leads to the conclusion that repolarization of the cardiac muscle cells is improved, with reduced cardiac infarction.

In addition to the pyrazolone derivatives to be employed according to the invention, the medicaments according to the present invention also contain pharmaceutically acceptable diluents or excipients. By these, there are to be understood non-toxic substances which, after being mixed with the active compound, render the active compound in a form suitable for administration. The term preferably excludes water and organic solvents of low molecular weight usually employed in chemical synthesis, apart from when other pharmaceutically required constituents are present, such as salts in the correct amounts to prepare an isotonic formulation, buffers, surface-active agents, colorants and flavoring agents and preservatives. The following substances are examples of suitable solid and liquid diluents and excipients: water-containing buffers which can be rendered isotonic by the addition of glucose or salts; non-toxic organic solvents, such as paraffins, vegetable oils, alcohols and glycols; ground natural rock materials (for example kaolins, aluminum oxides, talc or chalk); synthetic rock powders (for example highly disperse silicic acid or silicates); sugars; and aqueous suspensions of cellulose derivatives, for example methylhydroxyethylcellulose (Tylose).

The medicaments according to the invention as a rule contain 0.5 to 95% by weight, preferably 1 to 90% by weight and particularly preferably 5 to 50% by weight, of the pyrazolone derivatives to be employed according to the invention.

Oral administration can be effected using solid and liquid dosage forms, such as powders, tablets, dragees, capsules, granules, suspensions, solutions and the like. If desired, the dosage units can be microencapsulated for oral administration, in order to delay release or to slow it down over a longer period, such as, for example, by coating or embedding particulate material in polymers, wax or the like.

Parenteral administration can be effected using liquid dosage forms, such as sterile solutions and suspensions, which are intended for subcutaneous, intramuscular or intravenous injection. These dosage forms are prepared by suspending or dissolving a measured amount of the active compound in a non-toxic liquid extender suitable for injection, such as an aqueous or oil medium, and sterilizing the suspension or solution. Stabilizers, preservatives and emulsifiers can likewise be added.

In general, the daily dose of active compound for humans, based on the body weight, is 0.01 to 50 mg/kg, preferably 0.1 to 10 mg/kg, for parenteral administration and 0.5 to 500 mg/kg, preferably 0.5 to 100 mg/kg and particularly preferably 1 to 50 mg/kg, for oral administration.

The dosage unit (tablet, capsule and the like) as a rule contains 1 to 100 mg, preferably 5 to 50 mg and particularly preferably 10 to 30 mg, of the pyrazolone derivatives to be employed according to the invention.

EXAMPLE 1

Lipoxygenase-inhibiting action

The human PMN leucocytes (>95%) used in the present example were obtained from heparinized complete blood by dextran sedimentation and subsequent density gradient separation (Ficoll-Paque) (compare A. Boyum, Scand. J. Immunol., 5, Suppl. 5, 9, 1976).

$2 \times 10^7$ cells/ml were suspended in Dulbecco phosphate buffer containing $Ca^{2+}$ and were incubated with radioactively labelled arachidonic acid and the calcium ionophor A 23187 in the presence or absence of lipoxygenase inhibitor. After 15 minutes, the labelled lipoxygenase products were extracted from the acidified incubation medium and were separated by thin layer chromatography using a mobile phase mixture suitable for the leukotrienes (5-HETE-LTB$_4$) (compare B. Jakschik et al., Biochem. Biophys. Res. Commun., 102, 624, 1981).

The distribution of the activity amongst the various metabolites was measured by a thin layer scanner. It is a measure of the lipoxygenase-inhibiting action of a test substance at a certain concentration.

The lipoxygenase metabolites were also additionally determined independently by means of high pressure liquid chromatography. This method enables the endogenous arachidonic acid metabolism to be studied with the aid of UV detection of the leukotrienes. In this method, the cells were treated as described above, with the exception that no radioactively labelled arachidonic acid was added exogenously. The high pressure liquid chromatography was carried out on Lichrosorb RP-18 (5 μm) columns. The mobile phase was methanol/water/glacial acetic acid 69/31/0.01. The flow rate was 1 ml/minute. Leukotriene B$_4$ was determined at 280 nm and the HETE derivatives were determined at 232 nm, in each case by means of UV absorption.

The inhibition of LTB$_4$ biosynthesis by various pyrazolone derivatives is shown in Table 1 which follows:

TABLE 1

| Compound | Concentration (g/ml) | Inhibition (%) |
|---|---|---|
| [naphthalen-2-yloxy-CH₂-CH₂-N pyrazolinone with CH₂-CH(CH₃)₂] | $10^{-5}$<br>$5.10^{-6}$<br>$10^{-6}$<br>$5.10^{-7}$ | 100<br>100<br>100<br>89 |
| [naphthalen-1-yloxy-CH₂-CH₂-N pyrazolinone with CH₃] | $10^{-5}$<br>$5.10^{-6}$<br>$10^{-6}$<br>$5.10^{-7}$ | 100<br>87<br>62<br>-30 |
| [5-Br-naphthalen-2-yloxy-CH₂-CH₂-N pyrazolinone with C₂H₅ and CH₃] | $10^{-5}$<br>$5.10^{-6}$<br>$10^{-6}$ | 100<br>100<br>100 |
| [biphenyl-O-CH₂-CH₂-N pyrazolinone with CH₃] | $10^{-5}$<br>$5.10^{-6}$<br>$10^{-6}$<br>$5.10^{-7}$ | 100<br>100<br>75<br>63 |
| [5-Br-naphthalen-2-yloxy-CH₂-CH₂-N pyrazolinone with CH₃ and (CH₂)₃—CH₃] | $10^{-5}$<br>$5.10^{-6}$<br>$10^{-6}$<br>$5.10^{-7}$ | 100<br>87<br>68<br>31 |
| [5-Br-naphthalen-2-yloxy-CH₂-CH₂-N pyrazolinone with CH₃ and C₂H₅] | $10^{-5}$<br>$5.10^{-6}$<br>$10^{-6}$<br>$5.10^{-7}$ | 100<br>100<br>100<br>82 |
| [3,4-dichlorophenyl-CH(CH₃)-N pyrazole with CH₃ and O-CO-naphthyl] | $10^{-5}$ | 46 |

TABLE 1-continued

| Compound | Concentration (g/ml) | Inhibition (%) |
|---|---|---|
| [naphthalene-O-CH₂-CH₂-N(pyrazolone with CH₃, CH₃)] | $10^{-5}$ $5 \cdot 10^{-6}$ $10^{-6}$ $5 \cdot 10^{-7}$ | 100 100 83 75 |
| [naphthalene-O-CH₂-CH₂-N(pyrazolone with CH₃, (CH₂)₅—CH₃)] | $10^{-5}$ $5 \cdot 10^{-5}$ $10^{-6}$ | 100 100 93 |
| [phenyl-CH₂-CH₂-CH₂-N(pyrazolone with C₆H₅)] | $10^{-5}$ $5 \cdot 10^{-6}$ $10^{-6}$ | 100 100 81 |
| [phenyl-CH₂-CH₂-CH₂-N(pyrazolone with cyclohexyl, H)] | $10^{-5}$ $5 \cdot 10^{-6}$ $10^{-6}$ | 100 92 71 |
| [4-Cl,3-CH₃-phenyl-O-CH₂-CH₂-N(pyrazolone with CH₃)] | $10^{-5}$ $5 \cdot 10^{-6}$ $10^{-6}$ | 100 92 43 |
| [3,4-diCl-phenyl-CH(CH₃)-N(pyrazolone with CH₃, CH₂-C₆H₅)] | $10^{-5}$ $5 \cdot 10^{-6}$ | 100 100 |
| [1-naphthyl-CH₂-CH₂-N(pyrazolone with CH₃)] | $10^{-5}$ $5 \cdot 10^{-6}$ $10^{-6}$ | 100 75 58 |

TABLE 1-continued

| Compound | Concentration (g/ml) | Inhibition (%) |
|---|---|---|
| [naphthyl-O-CH₂-CH₂-N(N=C(CH₃))C(O)- dimer structure with two naphthalene-pyrazole units] | $10^{-5}$ | 50 |
| [3,4-dichlorophenyl-CH(CH₃)-N-N=C(CH₃)-CH=C(O-C(=O)-C₆H₄-Cl) pyrazole] | $10^{-5}$ | 80 |
| [naphthyl-O-CH₂-CH₂-N—N=C(CH₂—OH)—pyrazolone] | $10^{-5}$<br>$5.10^{-6}$ | 80<br>61 |
| [naphthyl-O-CH₂-CH₂-N—N=C(CH₂—O—C(=O)—CH₃)—pyrazolone] | $10^{-5}$<br>$5.10^{-6}$<br>$10^{-6}$ | 82<br>52<br>36 |
| [naphthyl-O-CH₂-CH₂-N—N=C(CH₂—O—CH₃)—pyrazolone] | $10^{-5}$<br>$5.10^{-6}$<br>$10^{-6}$ | 93<br>80<br>40 |
| [naphthyl-O-CH₂-CH₂-N—N=C(CH₃)—pyrazolone] (Comparison) | $10^{-5}$<br>$5.10^{-6}$<br>$10^{-6}$<br>$5.10^{-7}$ | 100<br>100<br>58<br>30 |

EXAMPLE 2

Specific stimulation of prostacyclin synthesis

The specific PGI₂-stimulating action of the pyrazolone derivatives was shown in vitro in a mixture of microsomes from the seminal vesicles of sheep (RSVM) and the aortas of cattle (BAM) (compare F. Cottee et al., Prostaglandins, 14, 413, 1977). ³H-arachidonic acid was incubated with a mixture of RSVM and BAM in the presence of $3.10^{-5}$ g/ml of the pyrazolone derivative at 25° C. for 10 minutes. The reaction was stopped by acidification to pH 3.5. The fatty acid metabolites were extracted with ethyl acetate. The ethyl acetate was evaporated off under N₂, the residue was taken up in CH₃OH/CHCl₃ (1:1) and the mixture was discharged on thin layer chromatography plastic sheets. Separation was effected with a mobile phase mixture of ethyl acetate/glacial acetic acid/isooctane/H₂O (110:20:50:10;

organic phase) (P. Needleman et al., The Journal of Clinical Investigation 1978, 61, 839–849). The distribution of the radioactivity was measured by means of a radio scanner.

The table which follows shows the influence of the pyrazolone derivatives ($10^{-4}$ g/ml) on the synthesis of various prostaglandins in RSVM in comparison with the control experiment without an active compound:

TABLE 2

| Prostaglandin | Increase in concentration (in %) in comparison with the control | |
|---|---|---|
| | Compound 1 | Compound 2 |
| 6-Keto-PGF$_{1\alpha}$ | 300–400 | 250–300 |
| PGD$_2$ | 0 | 0 |
| PGE$_2$ | 0 | 0 |
| PGF$_{2\alpha}$ | 0 | 0 |

Compound 1

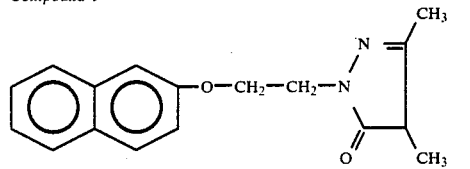

Compound 2

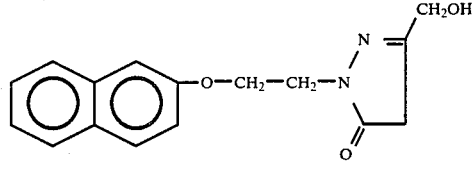

EXAMPLE 3

Leukocyte stickiness

The number of leucocytes which pass a certain section of a vessel serves as a simple model for measuring the stickiness of leucocytes (Bray, M. A. et al., Prostaglandins 22, 213 (1981)). The number of leucocytes counted will be greater, the lower the stickiness of the cells.

The pyrazolone derivatives described below were investigated in this model.

Male Syrian golden hamsters (80–100 g) were anaesthetized with Nembutal (i.p.; 60 mg/kg). After insertion of a PE 10 catheter into the a. femoralis, the animal was laid on a Duling dissecting platform (MVR 5, 423 (1973)) and the right cheek pouch was withdrawn by inserting a Q-Tip. It was carefully drawn into the envisaged part of the platform, stretched and fixed.

From the start of the dissection, 5 ml/minute of Superfusat flowedover the prepared cheek pouch. The temperature of the solution was 36° C. While treating the vessels with care, the upper layer tissue was separated longitudinally and folded back to the side. Under about 200-fold magnification, an area of about 1 cm$^2$ of connective tissue was carefully exposed. The animal was placed on the object stand of a microscope, together with the dissecting platform. A thermocouple was inserted into the left cheek pouch. The body temperature of the animal was thus monitored and kept at 36±0.3° C. with the aid of an IR lamp (250 watt).

The leucocyte stickiness was measured at about 500-fold magnification. A venule (30–40 μm φ) was selected in the exposed area. The number of leucocytes per unit time (minutes) which migrate past a certain section of this vessel were counted.

Intra-arterial administration of the pyrazolone derivatives in 1% strength aqueous Tylose suspension led to the following results:

TABLE 3

| Compound | Dose (mg/kg) | Increase in Leucocyte number (%) | Duration of action (minutes) |
|---|---|---|---|
| 1 | 0.1 | 75 | 30 |
| 2 | 1 | 25 | 30 |
| 3 | 1 | 200 | >>60 |
| 4 | 0.1 | 35 | 40 |
| 5 | 1 | 200 | 30–50 |
| 6 | 1 | 30 | 20–30 |

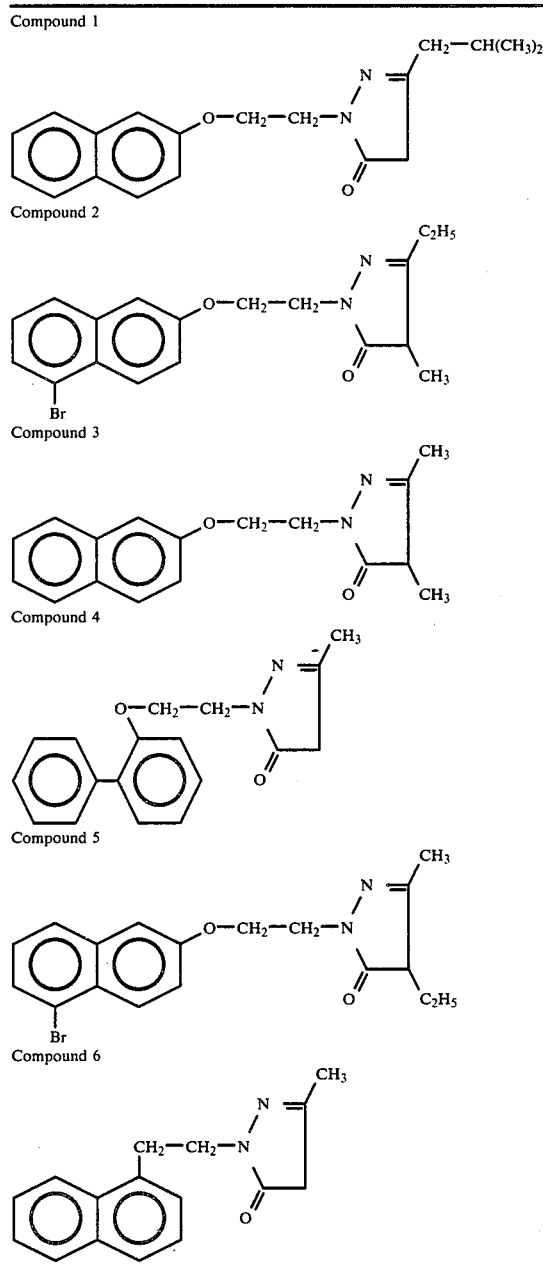

EXAMPLE 4

Action of the pyrazolone derivatives on rabbit hearts perfused by the method of Langendorff The heart was removed from the rabbits (up to about 2 kg) under Nembutal anaesthesia and cannulas were attached at the aorta and at the a. pulmonalis. To measure the isovolumetric contractions, a silicon rubber balloon filled with liquid was inserted into the left ventricle via the left auricle. The balloon was connected to a liquid sensor (Statham P 23 Db) via a liquid bridge. The perfusion pressure was recorded with a pressure sensor, which was connected to the perfusion system via a T-piece before the aorta cannula of the heart. The contraction force and perfusion pressure were recorded with a Gould 2600 S high-speed recorder. The hearts were stimulated electrically at a frequency of 180/minute and a stimulation duration of 5 mseconds.

Perfusion of the heart was effected with Krebs-Henseleit solution (KH solution), which was gassed with carbogen (95% of $O_2$, 5% of $CO_2$) or with a gas mixture of 2% of $O_2$, 5.6% of $CO_2$ and the remainder $N_2$. The perfusion volume was 20 ml/minute and was adjusted by a roller pump (Desaga, 132100). The pyrazolone derivatives (in 1% strength aqueous Tylose suspension) and the platelet suspensions (obtained from the same rabbit from which the heart was removed) were added with the aid of infusion pumps (roller pumps, Braun-Melsungen), the solution or suspension being infused at a flow rate of 0.2 or 0.1 ml/minute from an infusion syringe via a Taigon tube and a fine cannula into the inlet tube shortly before the heart.

The final concentration of the platelets was $1 \times 10^7$/ml of KH solution. The solution flowing out of the heart (cannula in the a. pulmonalis) was collected periodically, under ice-cooling. To measure the concentrations of thromboxan as $TXB_2$ and of prostacyclin as 6-keto-$PGF_1\alpha$, determination of which was effected with the aid of radioimmunoassay, aliquot parts by volume were freeze-dried and taken up in one tenth of the original volume of water.

The perfusion pressure values found in the experiments on administration of the active compound can be seen in comparison with those of the control in Table 4 which follows:

TABLE 4

| | Perfusion pressure in % of the blank value | | | | |
|---|---|---|---|---|---|
| | 1st phase | 2nd phase | 3rd phase | 4th phase | 5th phase |
| Control experiment | 100 | 155 | — | 83 | 214 |
| Compound 1 | 100 | 274 | 108 | 82 | 97 |

TABLE 4-continued

| | Perfusion pressure in % of the blank value | | | | |
|---|---|---|---|---|---|
| | 1st phase | 2nd phase | 3rd phase | 4th phase | 5th phase |
| Compound 2 | 100 | 176 | 107 | 83 | 103 |

1st phase - preliminary phase; gassing with carbogen
2nd phase - normoxia; gassing with carbogen; addition of $1.10^7$ platelets/ml; duration: 5 minutes
3rd phase - as 2nd phase; addition of $1.10^{-5}$ g/ml of pyrazolone derivative; duration: 5 minutes
4th phase - as 3rd phase, but gassing with only 2% of $O_2$ (hypoxia); duration: 10 minutes
5th phase - as 3rd phase (reoxygenation).

Compound 1

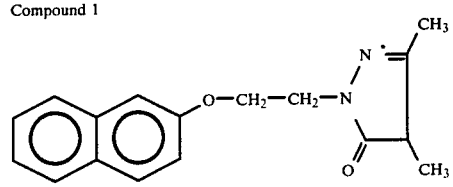

Compound 2

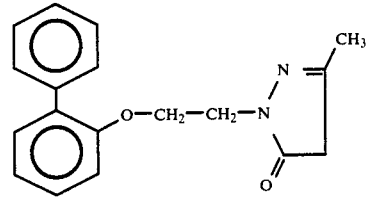

The results show that when platelets are added to the perfusion solution, there is a significant rise in the perfusion pressure in comparison with the preliminary phase. If perfusion is effected with a solution of low oxygen content (2% of $O_2$) in the subsequent phase, the perfusion pressure and the contraction force drop markedly. On subsequent reoxygenation (gassing with carbogen), the contraction force recovers to approximately the same values as before the period of hypoxia; however, the perfusion pressure rises beyond the pressure level in the first carbogen phase.

It is surprising that the pyrazolone derivatives to be employed according to the invention significantly inhibit the rise in perfusion pressure caused by addition of platelets to the perfusion solution in the first and second carbogen phase. This effect is particularly pronounced in the reoxygenation phase following the hypoxia phase.

EXAMPLE 5

Action of the pyrazolone derivatives on experimental cardiac infarction in dogs

The actions of various pyrazolone derivatives on experimental cardiac infarction was investigated in dogs after acute ligation of a coronary artery. In dogs anaesthetized with pentobarbital, the frontal descending left coronary artery (LAD) was slowly ligated proximally for 6 hours. The artery was no re-perfused. One hour before the ligature, the pyrazolone derivative was administered intraduodenally as a bolus in 1% strength aqueous tylose suspension. The control animals were treated in the same way, but without administration of the active compound. The infarction size and the perfusion area of the LAD were shown by a dual perfusion method with Evans blue and triphenyltetrazolium chloride. After the gradual, slow LAD ligation, the pyrazolone derivative substantially reduced the infarction. This was to be observed in respect of the absolute infarction rate and in respect of the infarction size in relation to the weight of the left ventricle. The perfusion areas of the ligated arteries were the same. The blodd pressure initially fell as a result of the coronary ligature, leading to a reflex increase in heart rate. Otherwise, no haemodynamic actions caused by pyrazolone derivatives were observed. The compounds reduced the infarction-induced increases in the ST segments and R waves of the peripheral ECG as signs of ischaemia, which lead to the conclusion that electrophysiological actions existed.

Literature:

Lucchesi et al., J. Pharmacol. Exp. Ther. 199: 310, 1978; and Fiedler, Basic Res. Cardiol. 78: 266, 1983.

The results are summarized in the tables which follow.

N number of dogs investigated in a particular experiment $N_1$ number of dogs killed by the ligature.

TABLE 5

| Compound | Mortality after 6 hours LAD ligature | | |
|---|---|---|---|
| | N | Dose (mg/kg) | Mortality ($N_1$) |
| 1 | 4 | 1 | 2 |
| | 4 | 3 | 0 |
| | 6 | 10 | 1 |
| 2 | 4 | 1 | 3 |
| | 4 | 3 | 0 |
| | 8 | 10 | 0 |
| 3 | 2 | 10 | 0 |

Compound 1:

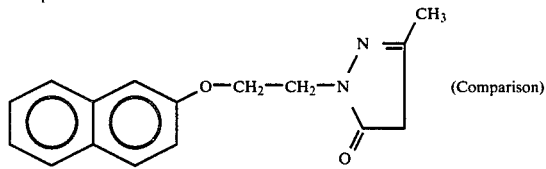

(Comparison)

Compound 2:

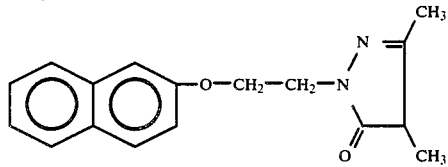

Compound 3:

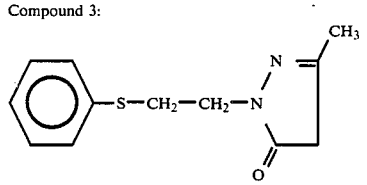

TABLE 6

| Time after which death occurs by vertricular fibrillation; a total of 4 hours LAD ligature | | | | |
|---|---|---|---|---|
| Compound | N | Dose (mg/kg) | $N_1$ | Death after |
| 1 | 5 | 10 | 2 | 14 minutes 23 seconds; 3 hours 37 minutes |
| | 4 | 3 | 2 | 25 minutes 40 seconds; 3 hours 21 minutes |
| | 4 | 1 | 3 | 24 minutes; 35 minutes; 2 hours 2 minutes |
| 2 | 8 | 10 | — | — |
| | 4 | 3 | — | — |
| | 4 | 1 | 2 | 2 hours 25 minutes; 3 hours 45 minutes |
| | 3 | 0.5 | 1 | 2 hours 16 minutes |

TABLE

| Size of the infarction after 6 hours LAD ligature | | | | |
|---|---|---|---|---|
| | | | Infarction size | |
| Dose | N | Weight of the left ventricle (g) | Weight (g) | % of the left ventricle |
| Control group | 8 | 97.3 ± 4.3 | 24.1 ± 3.4 | 24.8 ± 2.8 |
| 10 mg/kg of compound 2 | | 95.2 ± 3.2 | 12.1 ± 1.9 | 12.7 ± 2.1 |

It will be appreciated that the instant specification and examples are set forth by way of illustration and not limitation, and that various modifications and changes may be made without departing from the spirit and scope of the present invention.

We claim:

1. A method of inhibiting lipoxygenase in a patient having psoriasis, asthma, shock lung or oxygen intoxication, which comprises administering to such patient an effective amount of a compound of the formula

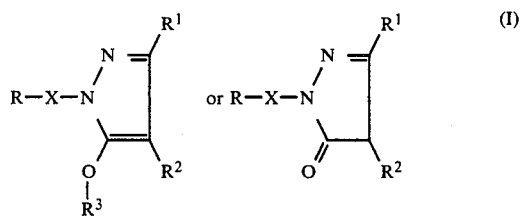

wherein

R represents an aryl or heteroaryl radical which has 6 to 12 C atoms and optionally contains 1 to 3 identical or different substituents from the group comprising halogen, trifluoromethyl, alkyl, alkenyl, alkoxy, alkylamino, cyano, trifluoromethoxy, nitro, hydroxyl, $SO_n$-alkyl (n=0 to 2) or $SO_n$-trifluoromethyl (n=0 or 2), alkyl, alkenyl and alkoxy in each case being understood as meaning radicals with 1 to 4 C atoms, $R^1$ represents hydrogen or a hydrocarbon radical which has 1 to 18 C atoms and optionally contains a hydroxyl, ether, ester or carbonyl group and optionally 1 to 3 halogen atoms, $R^2$ has the meaning of $R^1$ or represents a radical

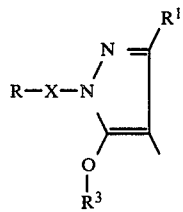

$R^3$ represents hydrogen or an acyl or sulphonyl radical with in each case 1 to 5 C atoms and X represents one of the groups —O—CH$_2$—CH$_2$—, —S—CH$_2$—CH$_2$—, —CH$_2$—CH$_2$—CH$_2$, —CH$_2$—CH$_2$—, —CH$_2$— or

the oxygen or sulphur atom being bonded to the radical R, and with the proviso that X does not represent —O—CH₂—CH₂— if R=β-naphthyl, R¹=CH₃ and R²=R³=H.

2. A method according to claim 1, in which R is naphthyl, diphenyl or phenyl radical which is optionally substituted once or twice by Cl or Br.

3. A method according to claim 1, in which R is an optionally substituted naphthyl radical.

4. A method according to claim 1, in which $R^1$ and $R^2$ each independently is hydrogen or a hydrocarbon radical which has 1 to 8 carbon atoms and optionally carries a hydroxyl, ether or ester group.

5. A method according to claim 1, in which each of $R^1$ and $R^2$ independently is an optionally branched $C_1$-$C_4$ alkyl group or one of them is hydrogen, $R^1$ and $R^2$ together containing 2 to 7 carbon atoms.

6. A method according to claim 1, in which $R^3$ is hydrogen or an aromatic acyl radical with 7 to 13 carbon atoms.

7. The method according to claim 1, in which the compound is

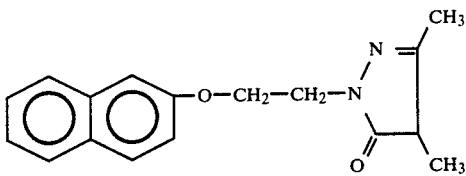

8. The method according to claim 1, where the patient has psoriasis and the compound is administered in an anti-psoriasis effective amount.

9. The method according to claim 1, wherein the patient has shock lung and the compound is administered in an anti-shock lung effective amount.

10. The method according to claim 1, where the patient has oxygen intoxication and the compound is administered in an anti-oxygen intoxication effective amount.

11. The method according to claim 1, where the patient has asthma and the compound is administered in an antiasthmatic effect amount.

* * * * *